United States Patent [19]

Preiss

[11] Patent Number: 5,095,112

[45] Date of Patent: Mar. 10, 1992

[54] PROCESS FOR THE PREPARATION OF QUINOLONECARBOXYLIC ACID ESTERS

[75] Inventor: Michael Preiss, Wuppertal, Fed. Rep. of Germany

[73] Assignee: Bayer Aktiengesellschaft, Leverkusen, Fed. Rep. of Germany

[21] Appl. No.: 121,502

[22] Filed: Nov. 17, 1987

[30] Foreign Application Priority Data

Dec. 5, 1986 [DE] Fed. Rep. of Germany ....... 3641661

[51] Int. Cl.⁵ ................ C07D 498/06; C07D 471/04; C07D 401/10; C07D 215/233

[52] U.S. Cl. .................................. 544/101; 544/344; 544/362; 544/363; 546/94; 546/123; 546/156

[58] Field of Search ...................... 546/156, 123, 94; 544/363, 362, 101, 344

[56] References Cited

FOREIGN PATENT DOCUMENTS 0131839 1/1985 European Pat. Off. ............ 546/156

OTHER PUBLICATIONS

Katritzky et al., "Advances in Heterocyclic Chemistry", vol. 17, p. 313 (1974).
Domagala, *Tetrahedron Letters*, 21, pp. 4997–5000 (1980).
Kim et al., *J. Org. Chem.* 50, p. 560 (1985).
Yim et al., Chemical Abstracts, vol. 109, No. 545279 (1988).

Primary Examiner—Mukund J. Shah
Assistant Examiner—E. Bernhardt
Attorney, Agent, or Firm—Sprung Horn Kramer & Woods

[57] ABSTRACT

A process for the preparation of quinolone-carboxylic acid esters of the formulae I and II

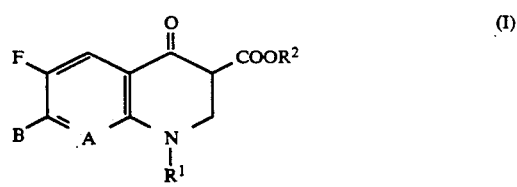
(I)

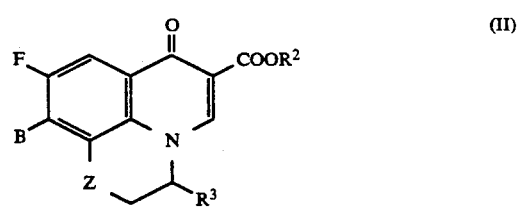

(II)

in which
A represents nitrogen or =C—R⁴,
R⁴ represents hydrogen, fluorine, chlorine, nitro or methyl,
B represents halogen, nitro, alkoxy, alkylsulphonyloxy or the radical

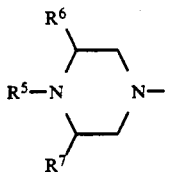

and B additionally represents

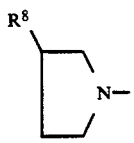

if R1 does not denote cyclopropyl, and
R⁵ represents a branched or unbranched alkyl group which has 1 to 4 carbon atoms and which can optionally be substituted by a hydroxyl or methoxy group,
R⁶ represents hydrogen, methyl or phenyl,
R⁷ represents hydrogen or methyl,
R⁸ represents dialkylamino having 1 or 2 carbon atoms in the alkyl group or dialkylaminomethyl having 1 or 2 carbon atoms in the alkyl group, or aminomethyl
R¹ represents hydrogen, optionally substituted alkyl having 1 to 3 carbon atoms, optionally substituted cycloalkyl, 2-fluoroethyl, vinyl, methoxy or 4-fluorophenyl,
R² represents optionally substituted alkyl having 1 to 6 carbon atoms and also cyclohexyl and benzyl,
R³ represents hydrogen, methyl or ethyl, and
Z represents oxygen, nitrogen which is substituted by methyl or phenyl, and =CH₂, characterized in that quinolonecarboxylic acids of the formulae III and IV

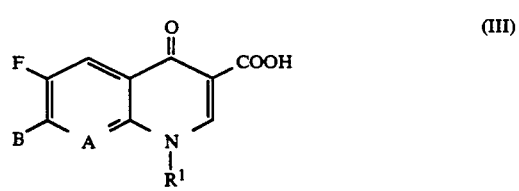
(III)

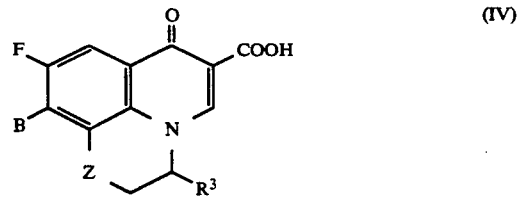

(IV)

in which A, B, Z, R¹ and R³ have the meanings indicated above, are reacted with chloroformic acid esters of the formula V Cl—COOR²     (V)

in which R² has the meaning indicated above.

12 Claims, No Drawings

PROCESS FOR THE PREPARATION OF QUINOLONECARBOXYLIC ACID ESTERS

The present invention relates to a process for the preparation of quinolonecarboxylic acid esters.

The acid-catalyzed esterification of carboxylic acids is known. In this reaction, the carboxylic acid is reacted with an alcohol in the presence of acids, and either the water formed is removed by azeotropic distillation or the equilibrium of the reaction is displaced by an excess of the alcohol In the case of quinolonecarboxylic acids, yields of only <50% can be achieved in this manner.

Although base-catalyzed esterification reactions of quinolonecarboxylic acids, for example by reacting the acid with an alkyl halide in the presence of a base, give yields of approximately 70 to 80%, they require the use of expensive reactive alkyl halides, in particular iodides, which, moreover, are carcinogenic.

The esterification of carboxylic acids with chloroformic acid esters is known In this case, however, there is formed as a by-product, above all when aromatic carboxylic acids are reacted, the symmetrical anhydride (S. Kim et al., Tetrahedron Letters 24 (1983), pages 3365-3368; A. L. Gutman et al., Tetrahedron Letters 26 (1985), pages 1573-1576; and S. Kim et al., J. Org. Chem. 1985 (50), pages 560-565).

It has now been found that quinolonecarboxylic acid esters of the formulae I and II

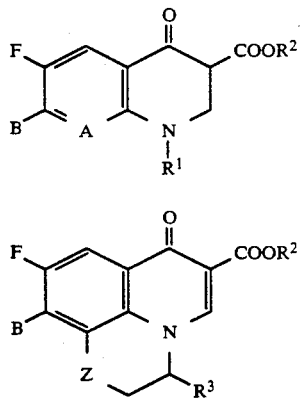

in which
A represents nitrogen or =C—R$^4$,
R$^4$ represents hydrogen, fluorine, chlorine, nitro or methyl,
B represents halogen, nitro, alkoxy, alkylsulphonyloxy or the radical

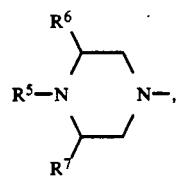

and B additionally represents

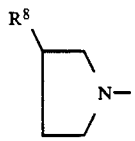

if R$^1$ does not denote cyclopropyl, and
R$^5$ represents a branched or unbranched alkyl group which has 1 to 4 carbon atoms and which can optionally be substituted by a hydroxyl or methoxy group,
R$^6$ represents hydrogen, methyl or phenyl,
R$^7$ represents hydrogen or methyl,
R$^8$ represents dialkylamino having 1 or 2 carbon atoms in the alkyl group or dialkylaminomethyl having 1 or 2 carbon atoms in the alkyl group, or aminomethyl,
R$^1$ represents hydrogen, optionally substituted alkyl having 1 to 3 carbon atoms, optionally substituted cycloalkyl, vinyl, methoxy or 4-fluorophenyl,
R$^2$ represents optionally substituted alkyl having 1 to 6 carbon atoms and also cyclohexyl and benzyl,
R$^3$ represents hydrogen, methyl or ethyl, and
Z represents oxygen, nitrogen which is substituted by methyl or phenyl, and also =CH$_2$,
are obtained by reacting quinolonecarboxylic acids of the formulae III and IV

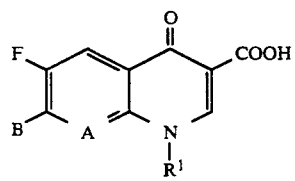

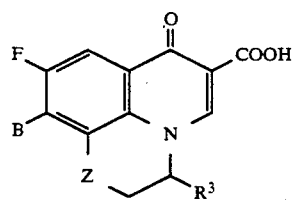

in which A, B, Z, R$^1$ and R$^3$ have the meanings indicated above, with chloroformic acid esters of the formula V

Cl—COOR$^2$ (V)

in which R$^2$ has the meaning indicated above.

It is preferable to prepare quinolonecarboxylic acid esters of the formula (VI)

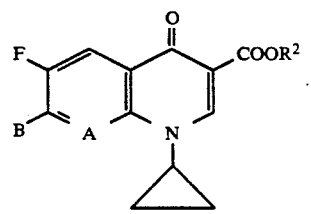

in which
B represents fluorine, chlorine or the radical

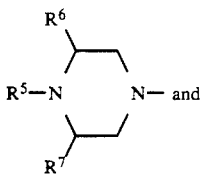

A, $R^2$, $R^5$, $R^6$, $R^7$ and $R^8$ have the meaning indicated above.

It is particularly preferable to prepare quinolonecarboxylic acid esters of the formula (VI)

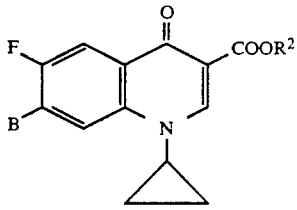

in which
$R^2$ represents alkyl having 1 to 4 carbon atoms, in particular ethyl, and also benzyl,
B represents the radical

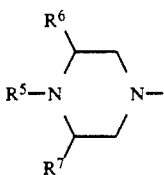

$R^5$ represents methyl or ethyl,
$R^6$ represents hydrogen or methyl and
$R^7$ represents hydrogen or methyl.

In particular, the methyl or ethyl esters of the following quinolonecarboxylic acids are prepared 1-Cyclopropyl-6-fluoro-1,4-dihydro-4-oxo-7-chloroquinoline-3-carboxylic acid, 1-cyclopropyl-6-fluoro-1,4-dihydro-4-oxo-7-fluoroquinoline-3-carboxylic acid, 1-cyclopropyl-6-fluoro-1,4-dihydro-4-oxo-7-(4-methyl-1-piperazinyl)-quinoline-3-carboxylic acid, 1-cyclopropyl-6-fluoro-1,4-dihydro-4-oxo-7-(4-ethyl-1-piperazinyl)-quinoline-3-carboxylic acid, 1-ethyl-6-fluoro-1,4-dihydro-4-oxo-7-(4-methyl-1-piperazinyl)-quinoline-3-carboxylic acid, 1-ethyl-6-fluoro-1,4-dihydro-4-oxo-7-chloroquinoline-3-carboxylic acid, 1-ethyl-6-fluoro-1,4-dihydro-4-oxo-7-(4-ethyl-1-piperazinyl)-1,8-naphthyridine-3-carboxylic acid and 9-fluoro-3-methyl-10-(4-methyl-1-piperazinyl)-7-oxo-2,3-dihydro-7,4-pyrido[1,2,4-de]1,4-benzoxazine-6-carboxylic acid.

It is preferable to employ chloroformic acid esters of the formula V in which $R^2$ represents $C_{1-4}$-alkyl which is optionally substituted by phenyl, halogen or OH. $R^2$ particularly preferentially represents $C_{1-4}$-alkyl, in particular methyl or ethyl.

Bases which may be mentioned are inorganic and organic bases. Inorganic bases are alkali metal hydroxides, carbonates and bicarbonates and alkaline earth metal hydroxides, carbonates and bicarbonates. Examples of organic bases are primary, secondary and tertiary amines. Tertiary amines are particularly preferred. The following may be mentioned Triethylamine, pyridine, picolines, trimethylamine, N-methylmorpholine, N-ethylpyrrolidine, diazabicyclo(4,3,0)undecene (DBU), 1,4-diazabicyclo-2,2,2-octane (DABCO) and diazabicyclo(3,2,0)nonene (DBN).

The reaction is carried out in the presence of halogenated aliphatic hydrocarbons having 1 to 4 C atoms and 1 to 5 halogen atoms. The following may be mentioned as examples: chloroform, methylene chloride, dichloroethane, trichloroethylene and carbon tetrachloride. Chloroform is particularly preferred.

The reaction is carried out at temperatures from −50° C. to 0° C., preferably at −20° C. to −15° C.

The reaction is carried out under normal pressure.

The chloroformic acid esters of the formula V are employed in equimolar amounts or in an excess of 5 to 30%, relative to the quinolonecarboxylic acids of the formulae III and IV. An excess of approximately 20% by weight is preferred The bases are employed in equimolar amounts, relative to the quinolonecarboxylic acids of the formulae III and IV. In the case of tertiary organic amines it is possible to carry out the reaction using a molar excess of 5 to 30%, preferably 10%.

The reaction according to the invention is carried out by first dissolving the quinolonecarboxylic acids of the formulae III and IV in an anhydrous aliphatic, halogenated hydrocarbon and adding the base. The mixture is cooled to approximately −20° C., and the chloroformic acid ester is added dropwise, with cooling, at this temperature. Stirring is continued at −20° C. and the temperature is then slowly raised to room temperature. Water is then added to the reaction mixture and it is worked up in a customary manner.

The quinolonecarboxylic acid esters of the formulae I and II are well known bactericides and microbicides.

EXAMPLE 1

Ethyl 1-cyclopropyl-6-fluoro-1,4-dihydro-4-oxo-7-(4-ethyl-1-piperazinyl)-3-quinolinecarboxylate 100 parts by weight of 1-cyclopropyl-6-fluoro-1,4-dihydro-4-oxo-7-(4-ethyl-1-piperazinyl)-3-quinolinecarboxylic acid were dissolved in 300 parts by volume of anhydrous chloroform, and 33.2 parts by weight of triethylamine were added. A solution of 37.7 parts by weight of ethyl chloroformate in 100 parts by volume of anhydrous chloroform was added dropwise to this mixture at −20° C. in the course of 30 minutes, and the mixture was stirred for a further 30 minutes at −20° C. and was then stirred overnight at room temperature. After extraction with twice 300 parts by volume of water, 400 parts by volume of water were added to the organic phase. The pH was adjusted to 5 with glacial acetic acid (consumption approximately 15 parts by volume), and the chloroform was removed by distillation under a water pump vacuum. The pH of the aqueous solution was adjusted to 8.9 with half-concentrated potassium hydroxide solution (consumption approximately 70 parts by volume), and the mixture was stirred overnight at room temperature. The product was filtered off with suction, washed with 500 parts by volume of water and dried overnight at 70° C. in a vacuum drying cabinet.

Yield: 103.2 parts by weight (95.7% of theory), melting point 183° to 185° C.

Content (HPLC): 98.8% area.

It will be appreciated that the instant specification and claims are set forth by way of illustration and not limitation, and that various modifications and changes may be made without departing from the spirit and scope of the present invention.

What is claimed is:

1. A process for the preparation of a quinolonecarboxylic acid ester of the formulae I or II

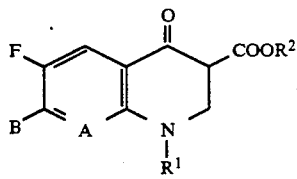
(I)

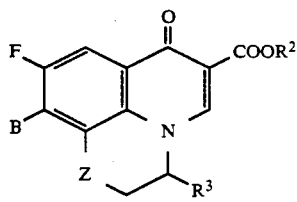
(II)

in which

A represents nitrogen or $=C-R^4$, $R^4$ represents hydrogen, fluorine, chlorine, nitro or methyl, B represents halogen, nitro, alkoxy, alkylsulphonyloxy or the group

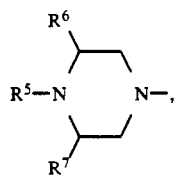

and B additionally represents

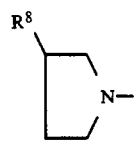

if $R^1$ does not denote cyclopropyl, and $R^5$ represents a branched or unbranched alkyl group which has 1 to 4 carbon atoms and which is unsubstituted or substituted by a hydroxyl or methoxy group, $R^6$ represents hydrogen, methyl or phenyl, $R^7$ represents hydrogen or methyl, $R^8$ represent dialkylamino having 1 to 2 carbon atoms in the alkyl group, dialkylaminomethyl having 1 or 2 carbon atoms in the alkyl group, or aminomethyl, $R^1$ represents hydrogen, alkyl having 1 to 3 carbon atoms, cycloalkyl, vinyl, methoxy or 4-fluorophenyl, $R^2$ represents alkyl having 1 to 6 carbon atoms and also cyclohexyl and benzyl, $R^3$ represents hydrogen, methyl or ethyl, and Z represents oxygen, nitrogen which is substituted by methyl or phenyl, or $=CH_2$, comprising reacting a quinolonecarboxylic acid of the formulae III

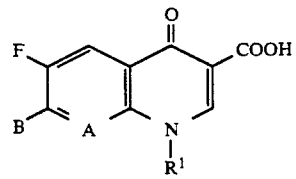
(III)

or the formula IV

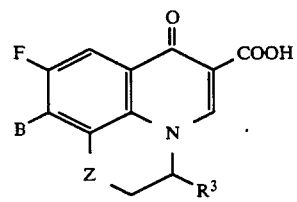
(IV)

in which

A, B, Z, $R^1$ and $R^3$ have the meanings indicated above, with a chloroformic acid ester of the formula V $$Cl-COOR^2 \qquad (V)$$

in which $R^2$ has the meaning indicated above, wherein the reaction mixture consists of said quinolonecarboxylic acid, said chloroformic acid ester, a tertiary amine selected from the group consisting of triethylamine, pyridine, picolines, trimethylamine, N-methylmorpholine, N-ethylpyrrolidine, diazabicyclo (4,3,0) undecene 1,4-diazabicyclo-2,2octane and diazabicyclo(3,2,0-)nonene, and a halogenated aliphatic hydrocarbon having 1 to 4 carbon atoms and 1 to 5 halogen atoms, wherein the process is carried out at a temperature of $-50°$ C. to $0°$ C. and wherein the chloroformic acid ester is employed in an equimolar amount or in an excess of 5 to 30% relative to the quinolonecarboxylic acid.

2. A process according to claim 1, wherein the quinolonecarboxylic acid ester is of the formula

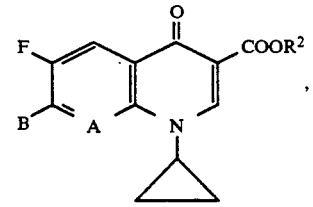

wherein

B represents fluorine, chlorine or the group

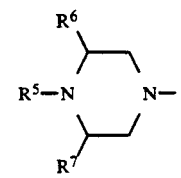

and

A, $R^2$, $R^5$, $R^6$, $R^7$ and $R^8$ have the meanings recited in claim 1.

3. A process according to claim 1, wherein the quinolonecarboxylic acid ester is of the formula

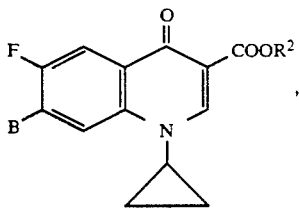

wherein
$R^2$ represents alkyl having 1 to 4 carbon atoms, and also benzyl,
B represents the group

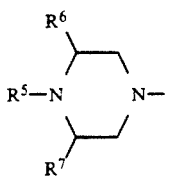

wherein
$R^5$ represents methyl or ethyl,
$R^6$ represents hydrogen or methyl and
$R^7$ represents hydrogen or methyl.

4. A process according to claim 1, wherein the quinolonecarboxylic acid ester is a methyl or ethyl ester of a carboxylic acid selected from the group consisting of
1-cyclopropyl-6-fluoro-1,4-dihydro-4-oxo-7-chloroquinoline-3-carboxylic acid, 1-cyclopropyl-6-fluoro-1,4-dihydro-4-oxo-7-fluoroquinoline-3-carboxylic acid, 1-cyclopropyl-6-fluoro-1,4-dihydro-4-oxo-7-(4-methyl-1-piperazinyl)-quinoline-3-carboxylic acid, 1-cyclopropyl-6-fluoro-1,4-dihydro-4-oxo-7-(4-ethyl-1-piperazinyl)-quinoline-3-carboxylic acid, 1-ethyl-6-fluoro-1,4-dihydro-4-oxo-7-(4-methyl-1-piperazinyl)-quinoline-3-carboxylic acid, 1-ethyl-6-fluoro-1,4-dihydro-4-oxo-7-chloroquinoline-3-carboxylic acid, 1-ethyl-6-fluoro-1,4-dihydro-4-oxo-7-(4-ethyl-1-piperazinyl)-1,8-naphthyridine-3-carboxylic acid and 9-fluoro-3-methyl-10-(4-methyl-1-piperazinyl)-7-oxo-2,3-dihydro-7,4-pyrido[1,2,4-de]1,4-benzoxazine-6-carboxylic acid.

5. A process according to claim 1, wherein $R^2$ in Cl—COOR$^2$ is $C_{1-4}$-alkyl which is unsubstituted or substituted by phenyl, halogen or OH.

6. A process according to claim 5, wherein $R^2$ is $C_{1-4}$-alkyl.

7. A process according to claim 6, wherein $R^2$ is selected from the group consisting of ethyl and methyl.

8. A process according to claim 1, wherein the reaction is carried out at a temperature of $-20°$ C. to $-15°$ C.

9. A process according to claim 1, wherein a molar excess of 5 to 30% of said tertiary amine to said quinolonecarboxylic acid is utilized.

10. A process according to claim 1, wherein the halogenated aliphatic hydrocarbon is selected from the group consisting of chloroform, methylene chloride, dichloroethane, trichloroethylene and carbon tetrachloride.

11. A process according to claim 1, wherein the base is triethylamine.

12. A process according to claim 10, wherein the halogenated aliphatic hydrocarbon is chloroform.

* * * * *

UNITED STATES PATENT AND TRADEMARK OFFICE
CERTIFICATE OF CORRECTION

PATENT NO. : 5,095,112

DATED : March 10, 1992

INVENTOR(S) : Michael Preiss

It is certified that error appears in the above-identified patent and that said Letters Patent is hereby corrected as shown below:

Title Page      OTHER PUBLICATIONS: Line 6 delete " 545279 " and substitute -- 54527q --

Title Page      ABSTRACT: Delete " 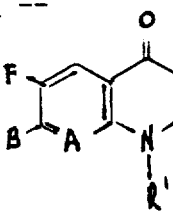 " and substitute

-- 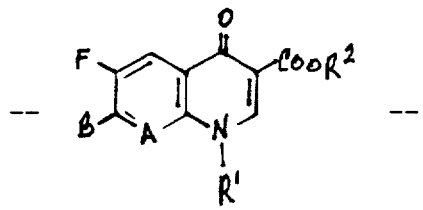 --

Col. 1, line 37    Delete " 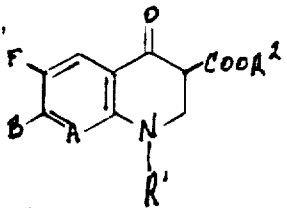 " and substitute

-- 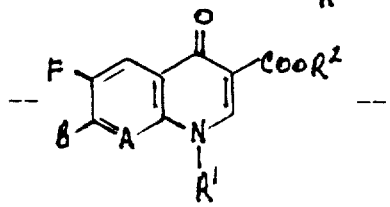 --

UNITED STATES PATENT AND TRADEMARK OFFICE
CERTIFICATE OF CORRECTION

PATENT NO. : 5,095,112

DATED : March 10, 1992

INVENTOR(S) : Michael Preiss

It is certified that error appears in the above-identified patent and that said Letters Patent is hereby corrected as shown below:

Col. 5, line 12   Delete " 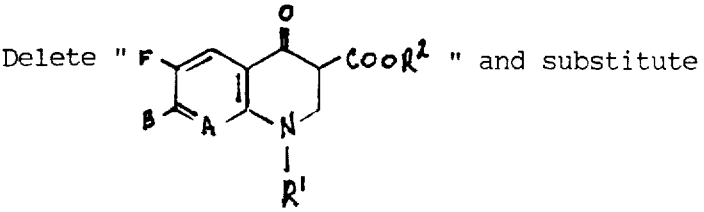 " and substitute

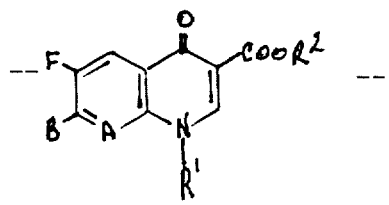 --

Col. 6, line 1    Delete " comprising " and substitute -- consisting of --

Col. 6, line 37   Delete " 2,2octane " and substitute -- 2,2,2-octane --

Signed and Sealed this

Twenty-first Day of December, 1993

*Attest:*

BRUCE LEHMAN

*Attesting Officer*   Commissioner of Patents and Trademarks